(12) United States Patent
Koh et al.

(10) Patent No.: US 11,571,435 B2
(45) Date of Patent: Feb. 7, 2023

(54) S1PR4-TARGETING COMPOSITION FOR PREVENTING OR TREATING NON-ALCOHOLIC STEATOHEPATITIS

(71) Applicants: UNIVERSITY OF ULSAN FOUNDATION FOR INDUSTRY COOPERATION, Ulsan (KR); THE ASAN FOUNDATION, Seoul (KR); SNU R&DB FOUNDATION, Seoul (KR)

(72) Inventors: Eunhee Koh, Seoul (KR); Kiup Lee, Gyeonggi-do (KR); Sanghee Kim, Seoul (KR); Daeduk Kim, Seoul (KR)

(73) Assignees: UNIVERSITY OF ULSAN FOUNDATION FOR INDUSTRY COOPERATION, Ulsan (KR); THE ASAN FOUNDATION, Seoul (KR); SNU R&DB FOUNDATION, Seoul (KR)

( * ) Notice: Subject to any disclaimer, the term of this patent is extended or adjusted under 35 U.S.C. 154(b) by 652 days.

(21) Appl. No.: 16/498,283

(22) PCT Filed: Mar. 29, 2018

(86) PCT No.: PCT/KR2018/003711
§ 371 (c)(1),
(2) Date: Sep. 26, 2019

(87) PCT Pub. No.: WO2018/182329
PCT Pub. Date: Oct. 4, 2018

(65) Prior Publication Data
US 2021/0100820 A1    Apr. 8, 2021

(30) Foreign Application Priority Data

Mar. 29, 2017  (KR) .................. 10-2017-0040139

(51) Int. Cl.
  A61K 31/661   (2006.01)
  A61K 31/4192  (2006.01)
  A61K 31/42    (2006.01)
  A61K 45/06    (2006.01)

(52) U.S. Cl.
  CPC ........ A61K 31/661 (2013.01); A61K 31/4192 (2013.01); A61K 31/42 (2013.01); A61K 45/06 (2013.01)

(58) Field of Classification Search
  CPC ................................................. A61K 31/661
  USPC ......................................................... 514/92
  See application file for complete search history.

(56) References Cited

U.S. PATENT DOCUMENTS

2016/0340321 A1*  11/2016  Hou ..................... C07D 249/04

FOREIGN PATENT DOCUMENTS

| EP | 3603636 A1 | 2/2020 |
|---|---|---|
| JP | 2019553451 | 4/2020 |
| JP | 6890805 B2 | 5/2021 |
| KR | 20170025909 A | 3/2017 |
| WO | 2004096757 A1 | 11/2004 |
| WO | 2008064320 A2 | 5/2008 |
| WO | 2009060053 A1 | 5/2009 |
| WO | 2010068775 A2 | 6/2010 |
| WO | 2014145873 A | 9/2014 |
| WO | 2018182329 A1 | 3/2018 |

OTHER PUBLICATIONS

Extended European Search Report for Application No. 18774760.5-1112/3603636 PCT/KR2018003711 dated Dec. 2, 2020.
Canadian Office Action for Application No. 3058124 dated Nov. 10, 2020.
Mauer, A.S. et al., "Inhibition of sphingosine 1-phosphate signaling ameliorates murine nonalcoholic steatohepatitis", Am J Physiol Gastrointest Liver Physiol, 312, pp. G300-G313, Dec. 30, 2016 (Dec. 30, 2016).
Leu, W-J. et al., "Non-immunosuppressive triazole-based small molecule induces anticancer activity against human hormone-refractory prostate cancers: The role in inhibition of PI3K/AKT/mTOR and c-Myc signaling pathways", Oncotarget-, 7, Pages 76995-77009, Oct. 19, 2016 (Oct. 19, 2016).
Yulin Tian, et al. "Discovery of oxazole and triazole derivatives as potent and selective S1P1 agonists through pharmacophore-guided design" European Journal of Medicinal Chemistry, 85, 1-15, 2014.
Korean Office Action for Application No. 9-5-2020-067815218 dated Oct. 5, 2020. No English Translation Available. Not considered. Must file English translation.
Office action issued by the Saudi Patent Office for corresponding application No. 519410204 dated Oct. 29, 2021.
Calzavara, "Investigations Into the Chemoselective Modification of Tham Directed Towards Biological Applications", McMaster University © Copyright by Janice Calzavara, Apr. 2012.

(Continued)

Primary Examiner — Taofiq A Solola
(74) Attorney, Agent, or Firm — Tarolli, Sundheim, Covell & Tummino LLP

(57) ABSTRACT

The present invention relates to a S1PR4-targeting composition for preventing or treating non-alcoholic steatohepatitis and, more particularly, to a pharmaceutical composition and a health functional food composition, both comprising a sphingolipid compound which serves as a functional inhibitor against S1PR4, showing prophylaxis and therapy of non-alcoholic steatohepatitis. The sphingolipid compound of the present invention is expected to be applied as a leading material effective for the prevention or treatment of non-alcoholic steatohepatitis (NASH) as it has the effect of reducing the infiltration of inflammatory cells into hepatic tissues and suppressing fibrosis and decreases a level of liver injury (ALT), inflammation in hepatic tissues, the expression of a fibrosis-related gene.

2 Claims, 10 Drawing Sheets

(56) References Cited

OTHER PUBLICATIONS

Leu, et al., "Non-immunosuppressive triazole-based small molecule induces anticancer activity against human hormone-refractory prostate cancers: the role in inhibition of PI3K/AKT/mTOR and c-Myc signaling pathways", www.impactjournais.com/oncotarget/ Oncotarget, vol. 7, No. 47.

Mauer, et al. "Inhibition of sphingosine 1-phosphate signaling ameliorates murine nonalcoholic steatohepatitis", Am J Physiol Gastrointest Liver Physiol 312: G300-G313, 2017. First published Dec. 30, 2016; doi:10.1152/ajpgi.00222.2016.

Tian, et al. "Discovery of oxazole and triazole derivatives as potent and selective S1P1 agonists through pharmacophore-guided design", European Journal of Medicinal Chemistry 85 (2014) 1-15.

Miller, et al., "RCAD/BiP pathway is necessary for the proper synthesis of digestive enzymes and secretory function of the exocrine pancreas" Jan. 19, 2017.

Australian Examination Report for Application No. 2018246796 dated Jul. 16, 2020.

Canadian Application No. 3,058,124; Title: S1PR4-Targeting Composition for Preventing or Treating Non-Alcoholic Steatohepatitis; Office Action dated Jun. 2, 2021; 4 pgs.

Mauer, A. S. et aL, "Inhibition of Sphingosine 1-phosphate Signaling Ameliorates Murine Nonalcoholic Steatohepatitis". American Journal of Physiology-, Gastrointestinal and Liver Physiology, 2017 [First published Dec. 30, 2016]. vol 312, pp. G300-G313 See p. 0300, right column, paragraph [2]; p. 0302, tables I, 2: and p. G312, left column, paragraph [2].

Tian, Y. et al., "Discovery of Oxazole and Triazole Derivatives as Potent and Selective S1 P1 Agonists through Pharmacophore-guided Design", European Journal of Medicinal Chemistry, 2014, vol. 85, pp. 1-15; See abstract and formulas I, 2.

Guo, J. et al., "Identification and Synthesis of Potent and Selective Pyridyl-isoxazole Based Agonists of Sphingosine-I-phosphate 1 (S1P1)", Bioorganic & Medicinal Chemistry Letters, 2016, vol. 26, pp. 2470-2474 See the entire document.

Kwong, E. et al., "Bile Acids and Sphingosine-1-phosphate Receptor 2 in Hepatic Lipid Metabolism", Acta Pharmaceutica Sinica B, 2015, vol. 5, No. 2, pp. 151-157 See the entire document.

Sato, M. et al., "Sphingosine Kinase-1, S1Ptransporter Spinster Homolog 2 and S1P:2 mRNA Expressions Are Increased in Liver with Advanced Fibrosis in Human", Scientific Reports, Aug. 26, 2016, vol. 6, No. 32119, pp. 1-8 See the entire document.

International Search Report for PCT/KR2018/003711.

\* cited by examiner

S1PR4-TARGETING COMPOSITION FOR PREVENTING OR TREATING NON-ALCOHOLIC STEATOHEPATITIS

RELATED APPLICATIONS

The present invention is a U.S. National Stage under 35 USC 371 patent application, claiming priority to Serial No. PCT/KR2018/003711, filed on 29 Mar. 2018; which claims priority of KR 10-2017-0040139, filed on 29 Mar. 2017, the entirety of both of which are incorporated herein by reference.

TECHNICAL FIELD

The present invention relates to an S1PR4-targeting composition for preventing or treating non-alcoholic steatohepatitis, and more particularly to a pharmaceutical composition and a nutraceutical (health functional food) composition for preventing or treating nonalcoholic steatohepatitis containing a sphingolipid compound which acts as a functional antagonist of S1PR4.

BACKGROUND ART

Myriocin, isolated from Cordyceps fungi, has been known for various pharmacological activities thereof for a long time and has been found to be effective in preventing the onset of non-alcoholic fatty acid liver disease (NAFLD) (Yang et al., Am. J. Physiol. Endocrinol. Metab. 2009; 19435851, Kurek et al., Liver Int. 2014; 24106929, Kasumov et al., PLos One. 2015; 25993337). However, experimentation on animals has shown that this substance caused death from severe digestive disorders at 10 times a normal dose due to the low safety margin thereof. For this reason, the substance has not developed into a drug. In addition, sphingolipid compounds containing myriocin have been considered to have low development potential as drugs due to the low solubility thereof in water.

However, FTY720 (Fingolimod) developed from myriocin derivatives has been approved to have an indication to relapsing-remitting multiple sclerosis (RRMS), which is a degenerative neurological disease that often occurs in western young people. Efforts to develop drugs based on sphingolipids are ongoing. FTY720 is an oral drug, which acts as a modulator of sphingosine 1-phosphate (S1P) receptors expressed in lymphocytes and various neuron cells on the immune system to reduce recycling and migration of pathogenic lymphocytes to the central nervous system.

Meanwhile, FTY720 acts non-selectively on subtypes of S1P receptors (S1P1, S1P2, S1P3, S1P4 and S1P5), resulting in problems due to lymphocyte reduction (lymphopenia) in blood or severe side effects centered in the cardiac circulatory system such as bradycardia and arrhythmia. Thus, there is a need for the development of a therapeutic agent having selectivity for the S1P receptor.

Therefore, as a result of extended efforts to develop an independent compound selectively acting on the S1P subtype receptor among sphingolipid compounds, the present inventors have found that the compound according to the present invention specifically binds to the S1P4 receptor present in macrophages and thus acts as a functional inhibitor (antagonist), thereby exerting effects of preventing or treating non-alcoholic steatohepatitis (NASH). Based on this finding, the present invention has been completed.

Technical Problem

Therefore, it is one object of the present invention to provide a pharmaceutical composition for preventing or treating nonalcoholic steatohepatitis.

It is another object of the present invention to provide a functional health food for preventing or treating nonalcoholic steatohepatitis.

Technical Solution

Therefore, the present invention has been made in view of the above problems, and provides a pharmaceutical composition for preventing or treating non-alcoholic steatohepatitis (NASH) containing a compound represented by the following formula 1, an optical isomer thereof or a pharmaceutically acceptable salt thereof as an active ingredient:

[Formula 1]

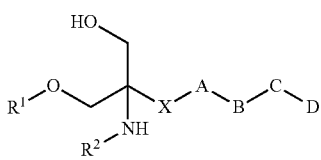

wherein
$R^1$ is hydrogen or

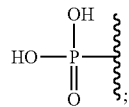

$R^2$ is hydrogen, or unsubstituted or substituted $C_{1-5}$ straight or branched alkyl carbonyl, wherein the substituted alkyl carbonyl is substituted with one or more substituents selected from the group consisting of hydroxy, halogen, cyano, nitro and amino;

A is a five-membered ring heteroarylene containing one or more heteroatoms selected from the group consisting of N, O and S;

B is $C_{1-11}$ straight or branched alkylene;
C is a single bond or $C_{6-10}$ arylene;
D is —H, or $C_{1-15}$ straight or branched alkyl; and
X is a single bond, $C_{1-5}$ alkylene, $C_{2-5}$ alkenylene or $C_{2-5}$ alkynylene.

Preferably, $R^1$ is hydrogen or

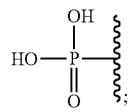

$R^2$ is hydrogen, or $C_{1-3}$ straight or branched alkyl carbonyl;

A is a five-membered ring heteroarylene containing one or more heteroatoms selected from the group consisting of N, O and S;

B is $C_{1-9}$ straight or branched alkylene;
C is a single bond or $C_{6-10}$ arylene;
D is —H, or $C_{3-12}$ straight or branched alkyl; and X is a single bond, $C_{1-3}$ alkylene, $C_{2-3}$ alkenylene or $C_{2-3}$ alkynylene.

More preferably, $R^1$ is hydrogen or

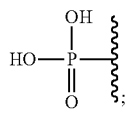

$R^2$ is hydrogen or acetyl;

A is a five-membered ring heteroarylene containing one or more heteroatoms selected from the group consisting of N, O and S;

B is $C_{2-8}$ alkylene;

C is a single bond or phenylene;

D is —H, or $C_{6-10}$ straight or branched alkyl; and

X is a single bond, —$CH_2CH_2$—, —CH=CH— or —C≡C—.

Preferred examples of the active ingredient represented by Formula 1 according to the present invention may include the following compounds:

(1) 2-amino-2-(2-(3-decylisoxazol-5-yl)ethyl)propane-1,3-diol;
(2) 2-amino-2-(2-(1-decyl-1H-1,2,3-triazol-4-yl)ethyl)propane-1,3-diol;
(3) 2-amino-2-((3-octylisoxazol-5-yl)ethynyl)propane-1,3-diol;
(4) 2-amino-2-(2-(3-octylisoxazol-5-yl)ethyl)propane-1,3-diol;
(5) 2-amino-2-(hydroxymethyl)-4-(3-octylisoxazol-5-yl)butyl dihydrogen phosphate;
(6) 2-amino-2-((3-decylisoxazol-5-yl)ethynyl)propane-1,3-diol;
(7) 2-amino-4-(3-decylisoxazol-5-yl)-2-(hydroxymethyl)butyl dihydrogen phosphate;
(8) 2-amino-2-(2-(3-(4-hexylphenethyl)isoxazol-5-yl)ethyl)propane-1,3-diol;
(9) 2-amino-2-((3-dodecylisoxazol-5-yl)ethynyl)propane-1,3-diol;
(10) 2-amino-2-(2-(3-dodecylisoxazol-5-yl)ethyl)propane-1,3-diol;
(11) 2-amino-4-(3-dodecylisoxazol-5-yl)-2-(hydroxymethyl)butyl dihydrogen phosphate;
(12) 2-amino-2-(2-(1-octyl-1H-1,2,3-triazol-4-yl)ethynyl)propane-1,3-diol;
(13) 2-amino-2-(2-(1-octyl-1H-1,2,3-triazol-4-yl)ethyl)propane-1,3-diol;
(14) 2-amino-2-((1-decyl-1H-1,2,3-triazol-4-yl)ethynyl)propane-1,3-diol;
(15) 2-amino-2-(2-(1-(4-hexylphenethyl)-1H-1,2,3-triazol-4-yl)ethyl)propane-1,3-diol;
(16) 2-amino-2-(1-butyl-1H-1,2,3-triazol-4-yl)propane-1,3-diol;
(17) 2-amino-2-(3-dodecylisoxazol-5-yl)propane-1,3-diol;
(18) (E)-2-amino-2-(2-(3-decylisoxazol-5-yl)vinyl)propane-1,3-diol;
(19) (E)-2-amino-2-(1-butyl-1H-1,2,3-triazol-4-yl)propane-1,3-diol;
(20) 2-amino-2-(2-(3-(8-phenyloctyl)-isoxazol-5-yl)ethyl)propane-1,3-diol;
(21) 2-amino-2-(2-(1-(8-phenyloctyl)-1H-1,2,3-triazole-butyl-4-yl)propane-1,3-diol;
(22) N-(2-(1-dodecyl-1H-1,2,3-triazol-4-yl)-1,3-dihydroxypropan-2-yl)acetamide;
(23) N-(2-(3-dodecylisoxazol-5-yl)-1,3-dihydroxypropan-2-yl)acetamide;
(24) N-(4-(1-decyl-1H-1,2,3-triazol-4-yl)-1-hydroxy-2-(hydroxymethyl)butan-2-yl)acetamide;
(25) N-(4-(3-decylisoxazol-5-yl)-1-hydroxy-2-(hydroxymethyl)butan-2-yl)acetamide; and
(26) N-(4-(1-(4-hexylphenethyl)-1H-1,2,3-triazol-4-yl)-1-hydroxy-2-(hydroxymethyl)butan-2-yl)acetamide.

The chemical structures of the compounds (1) to (26) are shown in Table 1 below.

TABLE 1

| No | Chemical structure |
|---|---|
| (1) | 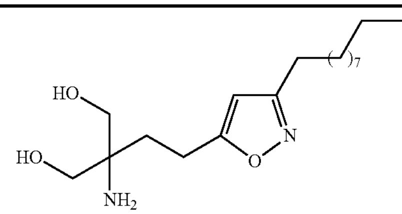 |
| (2) | 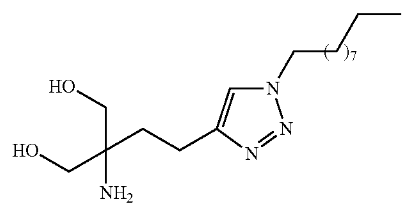 |
| (3) | 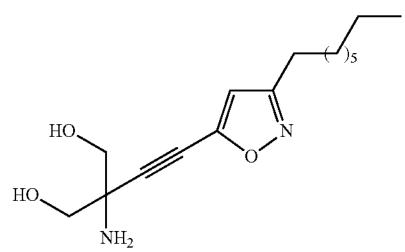 |
| (4) | 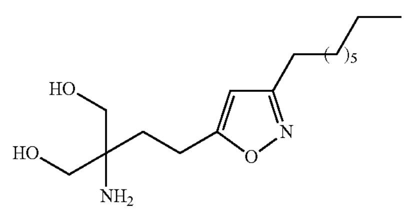 |
| (5) | 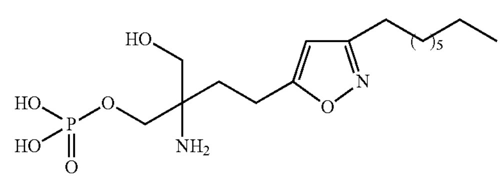 |
| (6) | 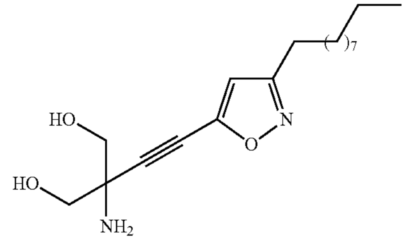 |

TABLE 1-continued

| No | Chemical structure |
|---|---|
| (7) | [structure: phosphate-substituted aminodiol with isoxazole and C8 chain] |
| (8) | [structure: aminodiol with isoxazole linked via ethylene to 4-hexylphenyl] |
| (9) | [structure: aminodiol with alkyne linked to isoxazole bearing C10 chain] |
| (10) | [structure: aminodiol with propylene linker to isoxazole bearing C10 chain] |
| (11) | [structure: phosphate-substituted aminodiol with isoxazole and C10 chain] |
| (12) | [structure: aminodiol with alkyne linked to 1,2,3-triazole N-substituted with C6 chain] |
| (13) | [structure: aminodiol with propylene linker to 1,2,3-triazole N-substituted with C6 chain] |
| (14) | [structure: aminodiol with alkyne linked to 1,2,3-triazole N-substituted with C8 chain] |
| (15) | [structure: aminodiol with ethylene linker to 1,2,3-triazole N-substituted with 2-(4-hexylphenyl)ethyl] |
| (16) | [structure: aminodiol directly bonded to 1,2,3-triazole N-substituted with C10 chain] |
| (17) | [structure: aminodiol directly bonded to isoxazole bearing C12H25 chain] |
| (18) | [structure: aminodiol with vinyl linker to isoxazole bearing C10H21 chain] |
| (19) | [structure: aminodiol with vinyl linker to 1,2,3-triazole N-substituted with C10H21 chain] |
| (20) | [structure: aminodiol with propylene linker to isoxazole bearing -(CH2)7-phenyl chain] |

TABLE 1-continued

| No | Chemical structure |
|---|---|
| (21) | 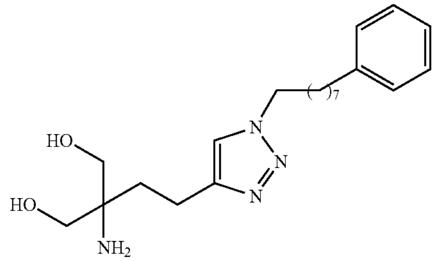 |
| (22) | 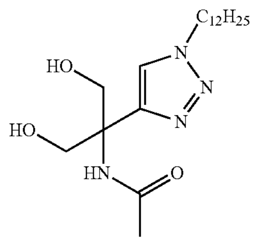 |
| (23) | 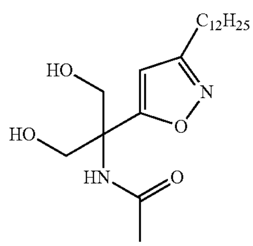 |
| (24) | 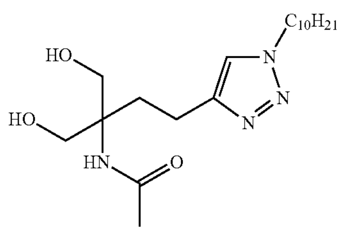 |
| (25) | 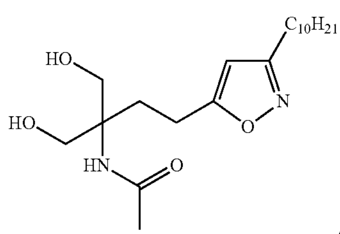 |
| (26) | 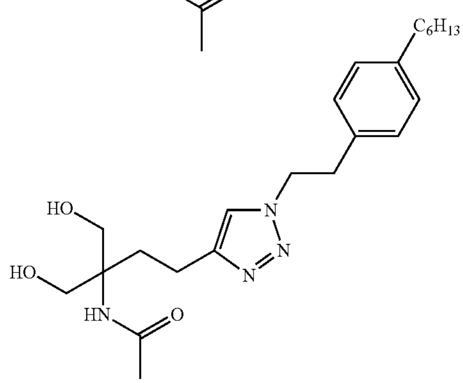 |

More preferably, the active ingredient according to the present invention is 2-amino-2-(2-(1-decyl-1H-1,2,3-triazol-4-yl)ethyl)propane-1,3-diol, which is a compound represented by the following Formula 2. In the following detailed description of the invention, the compound represented by the following Formula 2 is referred to as "SLB736".

[Formula 2]

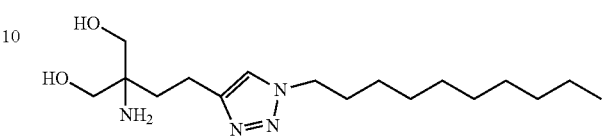

The compound represented by Formula 1 of the present invention may be used in the form of a pharmaceutically acceptable salt, and as the salt, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid and phosphorous acid, non-toxic organic acids such as aliphatic mono- and di-carboxylates, phenyl-substituted alkanoates, hydroxy alkanoates and alkane dioates, aromatic acids, aliphatic and aromatic sulfonic acids, and organic acids such as acetic acid, benzoic acid, citric acid, lactic acid, maleic acid, gluconic acid, methanesulfonic acid, 4-toluenesulfonic acid, tartaric acid and fumaric acid. Examples of the pharmaceutically nontoxic salt include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methyl benzoate, dinitrobenzoate, hydroxybenzoate, methoxybenzoate, phthalate, terephthalate, benzenesulfonate, toluenesulfonate, chlorobenzene sulfonate, xylene sulfonate, phenylacetate, phenylpropionate, phenylbutyrate, citrate, lactate, -hydroxybutyrate, glycolate, malate, tartrate, methane sulfonate, propane sulfonate, naphthalene-1 sulfonate, naphthalene-2-sulfonate, mandelate and the like.

The acid addition salt according to the present invention can be prepared through a conventional method, for example, by dissolving a derivative of Formula 1 in an organic solvent such as methanol, ethanol, acetone, methylene chloride or acetonitrile, adding an organic or inorganic acid thereto and filtering and drying the resulting precipitate, or distilling a solvent and excess acid under reduced pressure, drying and crystallizing the resulting product in an organic solvent.

Also, a pharmaceutically acceptable metal salt can be prepared using a base. An alkali metal or alkaline earth metal salt is, for example, obtained by dissolving the compound in an excess of an alkali metal hydroxide or alkaline earth metal hydroxide solution, filtering the insoluble compound salt, and evaporating and drying the filtrate. At this time, it is pharmaceutically suitable to prepare a sodium, potassium or calcium salt as the metal salt. Also, the corresponding salt is obtained by reacting an alkali or alkaline earth metal salt with a suitable silver salt (e.g., silver nitrate).

Furthermore, the present invention includes not only the compound represented by Formula 1 and pharmaceutically acceptable salts thereof, but also solvates, optical isomers, hydrates and the like that can be prepared therefrom.

As used herein, the term "prevention" refers to any action that inhibits or delays the onset of nonalcoholic steatohepatitis by administering the pharmaceutical composition of the present invention to a subject.

As used herein, the term "treatment" refers to any action that ameliorates or positively affects symptoms of nonalcoholic steatohepatitis by administering the pharmaceutical composition of the present invention to a subject.

The active ingredient of the present invention specifically binds to sphingosine 1-phosphate receptor 4 (S1PR4) and then removes the same in cells, thereby inhibiting the activity of S1PR4.

In addition, the active ingredient of the present invention inhibits the activity of the inflammation-regulatory complex (inflammasome).

In addition, the active ingredient of the present invention inhibits IL-β production in macrophages.

Specifically, as shown in FIG. 1, the compound of the present invention acts as a functional antagonist for this receptor, based on the mechanism of specifically binding to S1PR4 of macrophages and then inducing SIPR4 into cells and removing the same, thereby inhibiting the activity of NLRP3 inflammasome and preventing or treating nonalcoholic steatohepatitis (NASH).

The pharmaceutical composition of the present invention may further include a pharmaceutically acceptable carrier. In the present invention, the term "pharmaceutically acceptable" means that a compound is commonly used in the pharmaceutical field, while neither irritating an organism that administers the compound nor inhibiting the biological activity or properties of the administered compound.

In the present invention, the type of carrier is not particularly limited and any carrier can be used as long as it is commonly used in the art. Non-limiting examples of the carrier include saline, sterile water, Ringer's solution, buffered saline, albumin injection solutions, lactose, dextrose, sucrose, sorbitol, mannitol, xylitol, erythritol, maltitol, maltodextrin, glycerol, ethanol and the like. These may be used alone or in combinations of two or more thereof.

Also, the pharmaceutical composition of the present invention may be added with other pharmaceutically acceptable additives such as excipients, diluents, antioxidants, buffers or bacteriostatic agents, and may be optionally added with fillers, extenders, wetting agents, disintegrants, dispersants, surfactants, binders or lubricants.

The pharmaceutical composition of the present invention may be formulated into a variety of formulations suitable for oral or parenteral administration. Non-limiting examples of the formulation for oral administration include troches, lozenges, tablets, aqueous suspensions, oily suspensions, prepared powders, granules, emulsions, hard capsules, soft capsules, syrups or elixirs and the like.

In order to formulate the pharmaceutical composition for oral administration, a binder such as lactose, saccharose, sorbitol, mannitol, starch, amylopectin, cellulose or gelatin, an excipient such as dicalcium phosphate, a disintegrant such as corn starch or sweet potato starch, or a lubricant such as magnesium stearate, calcium stearate, sodium stearyl fumarate or polyethylene glycol wax may be used, and a sweetener, fragrance, syrup or the like may be also used.

Furthermore, in the case of a capsule, a liquid carrier such as fatty oil may be additionally used in addition to the above-mentioned substances.

Non-limiting examples of the parenteral formulation include injection solutions, suppositories, powders for respiratory inhalation, spray aerosols, ointments, powders for application, oils, creams and the like.

In order to formulate the pharmaceutical composition for parenteral administration, a sterile aqueous solution, a non-aqueous solvent, a suspension, an emulsion, a freeze-dried preparation, an external preparation and the like may be used. The non-aqueous solvent and the suspension may be propylene glycol, polyethylene glycol, vegetable oils such as olive oil, injectable esters such as ethyloleate or the like.

Further, more specifically, when the pharmaceutical composition of the present invention is formulated into an injection solution, the composition of the present invention is mixed in water with a stabilizer or buffer to prepare a solution or suspension, which is then formulated for ampoule or vial unit administration. In addition, when the pharmaceutical composition of the present invention is formulated into an aerosol, a propellant or the like may be combined with an additive so as to disperse the water-dispersed concentrate or the wet powder.

In addition, when the pharmaceutical composition of the present invention is formulated into an ointment, cream or the like, an animal oil, vegetable oil, wax, paraffin, starch, tragacanth, cellulose derivatives, polyethylene glycol, silicone, bentonite, silica, talc, zinc oxide or the like may be used as a carrier.

A pharmaceutically effective amount (effective dosage) of the pharmaceutical composition of the present invention may vary depending on the formulation method, administration method, administration time and/or administration route of the pharmaceutical composition or the like, and may vary depending on various factors including the type and extent of the response to be achieved by administering the pharmaceutical composition, the type, age, body weight, general state of health, state or extent of the disease, gender, diet, or excretion of the subject, to which the composition is administered, and the ingredients of drug compositions simultaneously or sequentially administered to the subject, as well as various similar factors well known in the pharmaceutical field, and those skilled in the art can easily determine and prescribe a dosage effective for the desired treatment.

The dosage of the pharmaceutical composition of the present invention to obtain more preferable effects is preferably 0.1 mg/kg to 1,000 mg/kg, more preferably 10 mg/kg to 500 mg/kg per day. The pharmaceutical composition of the present invention may be administered once a day, or may be administered several times in respective portions. Therefore, the dosage does not limit the scope of the present invention in any aspect.

The administration route and administration method of the pharmaceutical composition of the present invention may be independent of each other and are not particularly limited, and any administration route or method may be used, as long as the pharmaceutical composition can be delivered to the desired site. The pharmaceutical composition may be administered by oral or parenteral administration.

The method for parenteral administration includes, for example, intravenous administration, intraperitoneal administration, intramuscular administration, transdermal administration, subcutaneous administration or the like. The composition may be applied, sprayed or inhaled to the disease site, but the present invention is not limited thereto.

The present invention also provides a health functional food composition for preventing or ameliorating non-alcoholic steatohepatitis (NASH) containing the compound represented by Formula 1, an optical isomer thereof or a pharmaceutically acceptable salt thereof as an active ingredient.

The food composition of the present invention may be prepared into any one formulation selected from the group consisting of a tablet, granule, powder, capsule, liquid solution and pill. The food composition according to the present invention may be formulated into a powder, liquid, tablet, soft capsule, granule, tea bag, instant tea or drink containing the compound represented by Formula 1 as an active ingredient. The content of the active ingredient may be appropriately determined depending on the purpose of use (prevention or amelioration). In general, the amount of the active ingredient contained in the food composition may be added in an amount of 0.1 to 90% by weight of the total food weight. However, in the case of prolonged administration for health and hygiene or health maintenance, the amount may be below the range of content defined above. In addition, the food composition according to the present invention may also contain other pharmaceutical compositions or natural products that do not impair the main effect of the present invention in addition to the active ingredient described above and preferably have an effect synergistic with the main effect.

The food composition formulated in the form described above may be added to food as it is or may be used in combination with other food or food ingredients, and may be appropriately used according to conventional methods. Examples of the food include drinks, meat, sausages, bread, biscuits, rice cakes, chocolate, candies, snacks, confectionery, pizza, ramen, other noodles, gums, dairy products including ice creams, various soups, beverages, alcoholic beverages and vitamin complexes, dairy products and dairy-processed products, and include all functional foods in the conventional sense.

When the food composition of the present invention is a drink, it contains the active ingredient of the present invention as an essential ingredient in a predetermined ratio. There are no particular limitations as to other ingredients used to prepare the drink, and various flavoring agents or natural carbohydrates may be contained as additional components, like common beverages. Examples of such natural carbohydrates include conventional sugars including monosaccharides such as glucose and fructose, disaccharides such as maltose and sucrose and polysaccharides such as dextrin and cyclodextrin, and sugar alcohols such as xylitol, sorbitol and erythritol. In addition to the substances described above, a flavoring agent such as a natural flavoring agent or a synthetic flavoring agent may be used. The proportion of the natural carbohydrate is generally about 1 to 20 g, preferably about 5 to 12 g with respect to 100 ml of the composition of the present invention.

Also, the food composition of the present invention may contain a variety of nutrients, vitamins, minerals (electrolytes), flavoring agents such as synthetic flavoring agents and natural flavoring agents, colorings and enhancers (such as cheese or chocolate), pectic acid and salts thereof, alginic acid and its salts, organic acids, protective colloidal thickeners, pH adjusters, stabilizers, preservatives, glycerin, alcohols, carbonation agents used for carbonated drinks, and the like. In addition, the food composition of the present invention may contain flesh for producing natural fruit juices, fruit juice beverages and vegetable beverages. These components can be used independently or in combination. The proportion of such additives is not critical, but is generally determined within the range of about 0.1 to about 20 parts by weight with respect to 100 parts by weight of the active ingredient of the present invention.

The present invention also provides a pharmaceutical composition for preventing or treating nonalcoholic steatohepatitis containing a functional antagonist of S1PR4 as an active ingredient.

The present invention also provides a health functional food composition for preventing or ameliorating non-alcoholic steatohepatitis containing a functional antagonist of S1PR4 as an active ingredient.

In one embodiment of the present invention, the inhibition of S1PR4 expression through S1PR4 shRNA as well as the sphingolipid compound according to the present invention provides the effect of reducing IL-1β production in macrophages and the effects of preventing the onset of NASH and treating NASH. Therefore, the functional antagonist for S1PR4 according to the present invention may be not only a compound that acts as a functional antagonist against S1PR4 including the sphingolipid compound according to the present invention, but also the antibody against S1PR4 that inhibits the activity of S1PR4 protein, and antisense nucleotides, aptamers, siRNAs, shRNAs, miRNAs and RNAi for mRNA of S1PR4 that inhibits S1PR4 expression. In the present invention, the antibody against S1PR4 may be a monoclonal antibody or a polyclonal antibody.

The present invention also provides a method for preventing or treating nonalcoholic steatohepatitis (NASH) including administering to a subject a composition containing the compound represented by Formula 1, an optical isomer thereof, or a pharmaceutically acceptable salt thereof as an active ingredient.

The present invention also provides the use of composition containing the compound represented by Formula 1, an optical isomer thereof, or a pharmaceutically acceptable salt thereof as an active ingredient for preventing or treating nonalcoholic steatohepatitis (NASH).

Advantageous Effects

The sphingolipid compound of the present invention has effects of reducing deposition of lipids in liver tissue, reducing infiltration of inflammatory cells and inhibiting fibrosis, and is also expected to be applicable as a leading substance effective for the prevention or treatment of nonalcoholic steatohepatitis (NASH) by reducing liver function (ALT) levels, liver tissue inflammation and expression of fibrosis-related genes.

BRIEF DESCRIPTION OF THE DRAWINGS

The above and other objects, features and other advantages of the present invention will be more clearly understood from the following detailed description taken in conjunction with the accompanying drawings, in which.

BEST MODE

Hereinafter, the present invention will be described in more detail with reference to the following examples. However, it will be obvious to those skilled in the art that these examples are provided only for illustration of the present invention and should not be construed as limiting the scope of the present invention.

EXAMPLE 1

Selection of Sphingolipid Candidates

Fifteen types of sphingolipid compounds structurally similar to myriocin and FTY720 (fingolimod), among about 600 types of sphingolipid compounds held by a sphingolipid material bank, were obtained in order to develop lead candidates for the development of nonalcoholic steatohepatitis (NASH) drugs.

The result of measurement of agonistic activity of S1P receptors (sphingosine 1-phosphate receptors) using the GPCR activity measurement method of DiscoveRX Corp. showed that 2-amino-2-(2-(1-decyl)-1H-1,2,3-triazol-4-yl) ethyl)propane-1,3-diol (hereinafter referred to as "SLB736") has an agonistic effect specific for S1PR4.

[Formula 2]

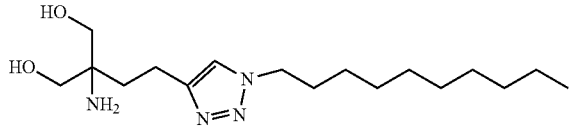

EXAMPLE 2

Inhibitory Activity of NLRP3 Inflammation-Regulating Complex

It is well known that the treatment of macrophages with lipopolysaccharide (LPS) results in activation of inflammation-regulating complex (inflammasome), thereby increasing IL-1β production (Mariathasan et al., Nat. Rev. Immunol. 2007; 17186029). In order to determine the inhibitory effect of the activity of inflammation-regulating complex (NLRP3 inflammasome), which is a representative inflammation-regulating protein, the IL-1(3 production of candidate substances upon the treatment of macrophages with LPS was measured and evaluated.

First, 12 hours after treatment of Raw cells (mouse macrophage lines) with LPS (100 ng/ml, Sigma-Aldrich), the concentration of IL-1β in the medium was found to be markedly increased.

The macrophages were treated with myriocin in different concentrations as a control group and were then treated with the same concentration of LPS for 24 hours. As a result, it was found that 10 μM of myriocin effectively reduced IL-1β production. Based on this, experiments were conducted to determine the effect of sphingolipid candidates on the inhibition of IL-1β.

Figure 1:
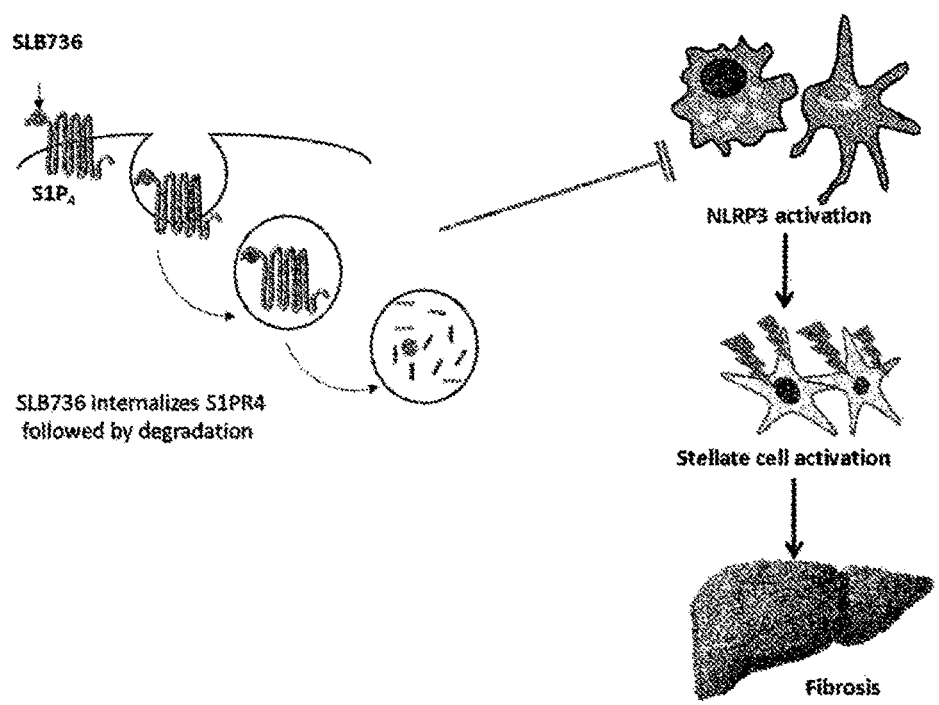
FIG. 1 is a schematic diagram showing a mechanism for treating nonalcoholic steatohepatitis of a compound according to the present invention.
Figure 2:
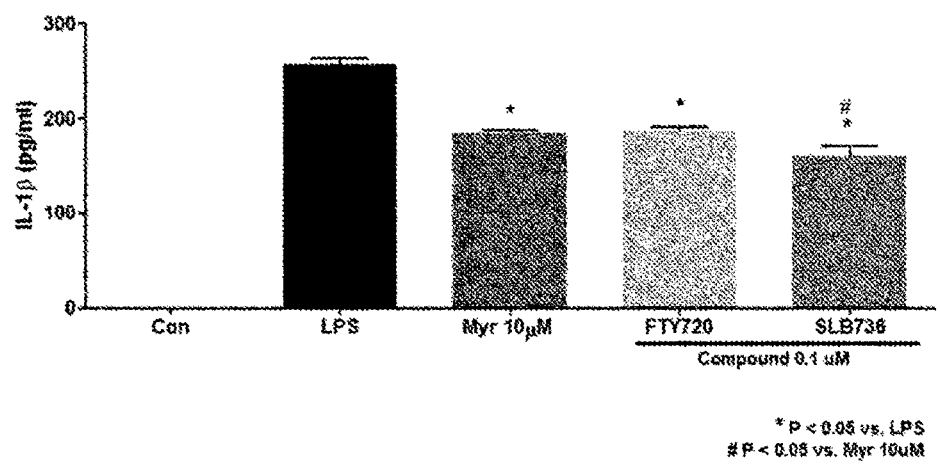
FIG. 2 shows the result identifying the inhibitory effect of the sphingolipid compound SLB736 according to the present invention on the activity of NLRP3 inflammation-regulating complex.
Figure 2:
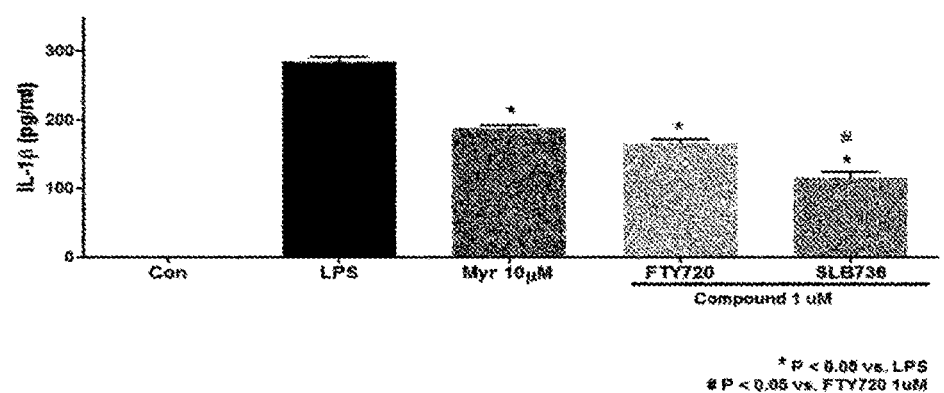

The result of treatment with the known sphingolipid derivative drug, FTY720, showed that FTY720 exhibits an inhibitory effect of IL-1β production similar to 10 μM myriocin at a concentration of 0.1 μM, which is a much lower concentration than myriocin. On the other hand, when treating with SLB736, the compound represented by Formula 2 according to the present invention, at 0.1 μM or 1.0 μM and then with LPS, it was found that the inhibitory effect of IL-1β production was excellent at each concentration to a significant extent to FTY720 (FIG. 2).

EXAMPLE 3

Identification of Effects of SLB736 on Inhibition of Expression of S1PR4 in Tissue and Cells In order to determine whether or not SLB736, the compound of the present invention, acts as a functional antagonist of S1PR4, changes in S1PR4 protein expression were observed after administration of candidate substances to nonalcoholic steatohepatitis (NASH) model mice and macrophages thereof.

Figure 3:
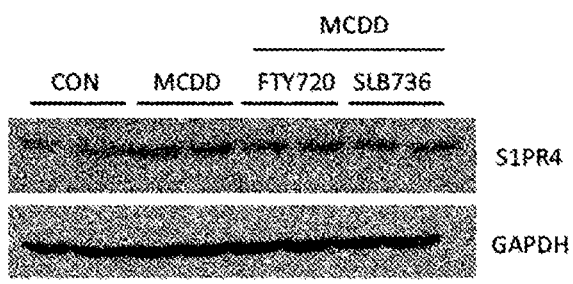
FIG. 3 shows the result identifying the inhibitory effect of the SLB736 compound according to the invention on S1PR4 expression in a mouse liver tissue model.

It is well known that the administration of a methionine choline-deficient diet (MCDD) to mice results in non-alcoholic steatohepatitis. The mice (C57BL/6N, Orient Bio, Inc., Korea) used in the experiments were divided into three groups, and MCDD alone, 1 mg/kg of MCDD and FTY720, and 1 mg/kg of MCDD and SLB736 were administered to each group for 6 weeks. Then, changes in the expression of S1PR4 protein in liver tissue of mice were measured through Western blotting. As a result, it was found that the expression of S1PR4 was significantly increased in the mice administered with MCDD alone compared to the control (con) mice not administered with MCDD, and the amount of S1PR4 protein was decreased in the mice administered with FTY720 or SLB736 in combination with MCDD (FIG. 3).

Figure 4:
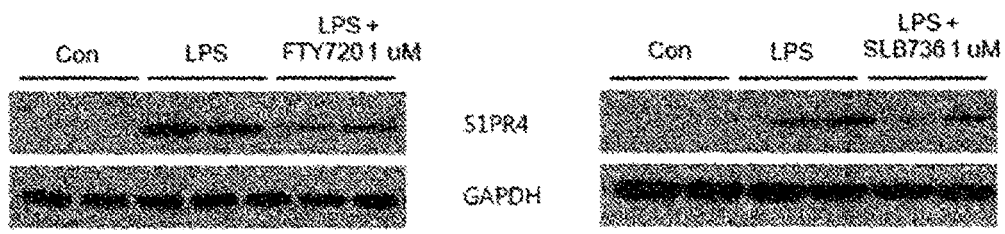
FIG. 4 shows the result identifying the inhibitory effect of the SLB736 compound according to the present invention on S1PR4 expression in a mouse macrophage model.

In addition, Raw cells, which are mouse macrophage lines, were treated with a FTY720 or SLB736 substance, and were then treated with LPS, and S1PR4 expression was then measured. As a result, the expression of S1PR4 was significantly increased in cells treated only with LPS, compared to the control group (con) without any treatment, whereas treatment with FTY720 or SLB736 in combination with LPS was found to significantly reduce the expression level of S1PR4 (FIG. 4).

This result demonstrates that the SLB736 compound of the present invention functions to reduce the expression level of S1PR4 protein.

EXAMPLE 4

Identification of Activity as Functional Antagonist of S1PR4

Cell lines overexpressing S1PR4-EGFP were used to identify whether or not SLB736 and FTY720 actually internalize S1PR4 into cells and thereby act as functional antagonists.

Specifically, the cell lines overexpressing S1PR4-EGFP were incubated in a cover glass allowing for microscopic observation and were then treated with a vehicle (dimethyl sulfoxide hydrochloric acid, 100 nM), S1P (100 nM; agonist, positive control group), FTY720 (100 nM) and SLB736 (1 µM). 30 minutes and 2 hours after treatment with each material, the cell lines were fixed with a fixing solution and observed with a fluorescence microscope. At this time, the cells were cultured after treatment with a protein synthesis inhibitor (cycloheximide) in order to inhibit the synthesis of new receptors, were first observed with a fluorescence microscope 30 minutes after each material treatment, and were then washed. Then, the cells were further cultured for 1 hour 30 minutes and were secondarily observed, and cell images were obtained.

Figure 5:
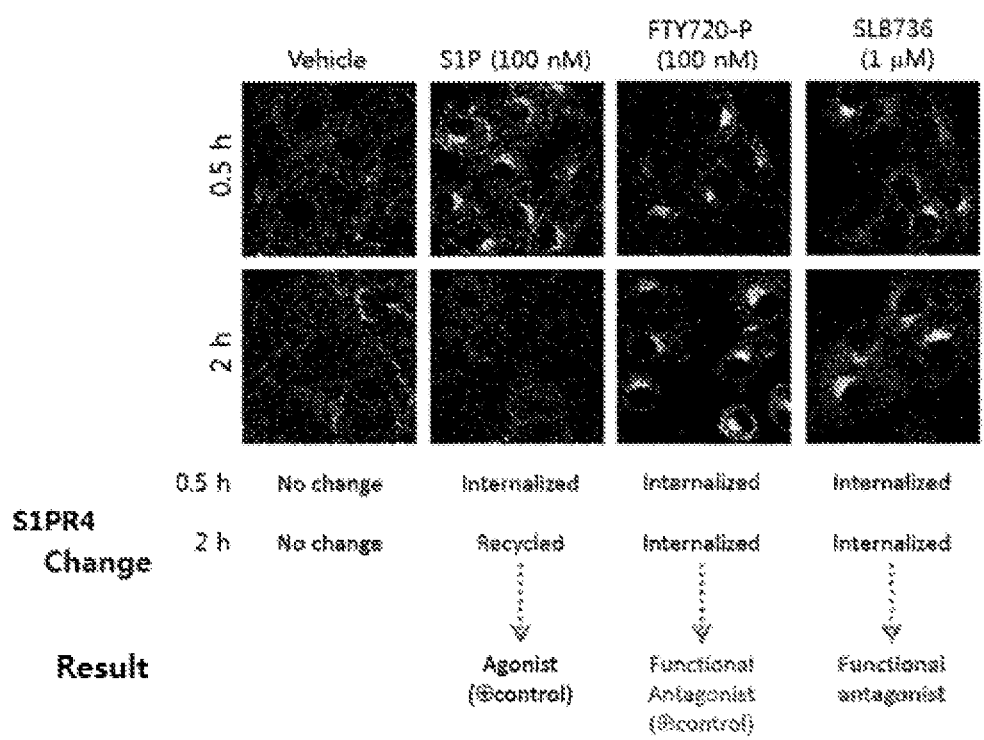
FIG. 5 shows the result identifying that the SLB736 compound of the present invention is not recycled to the cell membrane after being introduced into the cells.

The results are shown in FIG. 5. It could be seen that S1PR4 was internalized in the medium treated with S1P, FTY720 and SLB736 after cell culture for 30 minutes, and in S1P (agonist)-treated cells after cell culture for 2 hours, S1PR4 was recycled to the cell membrane, whereas FTY720 and SLB736 were not recycled thereto. This indicates that SLB736 according to the present invention acts as a functional antagonist of S1PR4, like FTY720.

EXAMPLE 5

Identification of Inhibition of IL-1β Production by S1PR4 shRNA

In addition, after infecting Raw cells, the macrophage line, with S1PR4 shRNA lentivirus, viable cells capable of inhibiting S1PR4 expression were selected. When treating the selected cells with LPS, changes in IL-1β production were measured and were compared with control groups (Vec, Vec+LPS) not infected with shRNA lentivirus.

Figure 6:
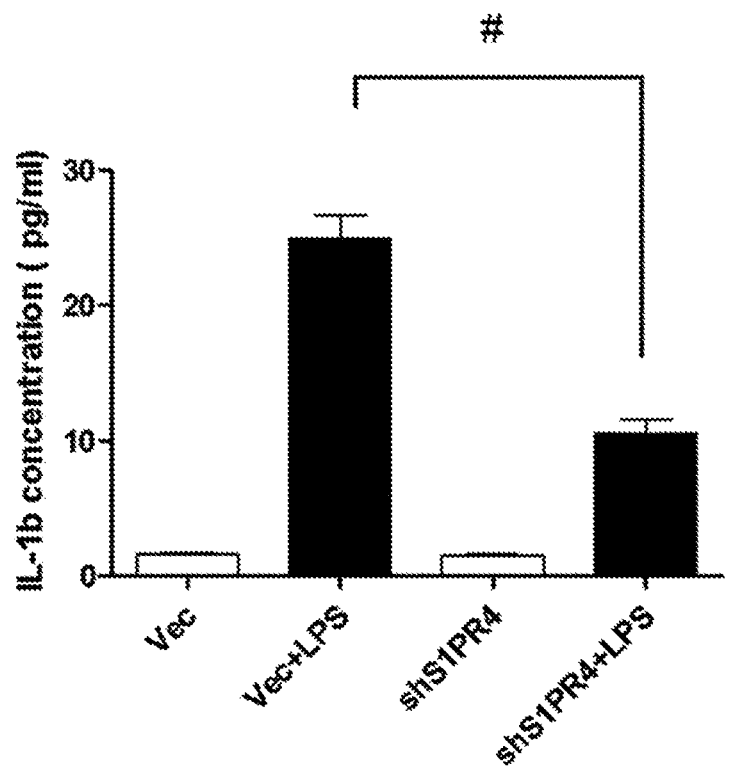
FIG. 6 shows the result identifying the inhibitory effect of reducing IL-β production of S1PR4 shRNA in mouse macrophages.

As a result, it could be seen from FIG. 6 that the IL-1β concentration was significantly reduced in the macrophage line infected with S1PR4 shRNA lentivirus (shS1PR4+LPS) compared to the control group (Vec+LPS).

EXAMPLE 6

Identification of Effects of SLB736 on Prevention of NASH Onset and Treatment of NASH In order to identify the effect of the SLB736 compound on the prevention of onset of non-alcoholic steatohepatitis (NASH), an animal model administered with MCDD for 6 weeks was used.

Generally known characteristic microscopic findings of NASH include steatosis, ballooning degeneration of hepatocytes, lobular inflammation, perisinusoidal fibrosis and the like. In 2005, the NASH clinical research network (CRN) designed a detailed grading system for lesions corresponding to nonalcoholic steatohepatitis and thus proposed the nonalcoholic fatty liver disease activity score (NAS), which is widely used in various research due to the excellent reproducibility thereof. Accordingly, the present inventors have scored the grade of steatosis, location of steatosis, lobular inflammation and the extent of fibrosis, from the results of liver tissue observation of animal models, based on the CRN classification system. Based on this, the effect of SLB736, which is the target compound in the present invention, on the prevention or progression of non-alcoholic steatohepatitis caused by MCDD was evaluated.

Figure 7:
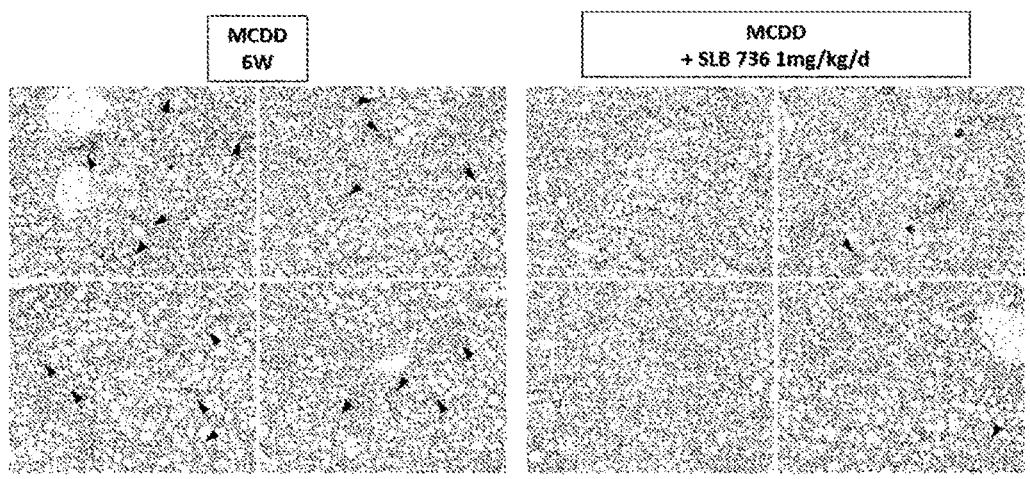
FIG. 7 shows the result of microscopic examination for identifying the effect of SLB736 on the prevention of steatosis and lobular inflammation in liver tissue of a NASH-induced mouse model.
Figure 8:
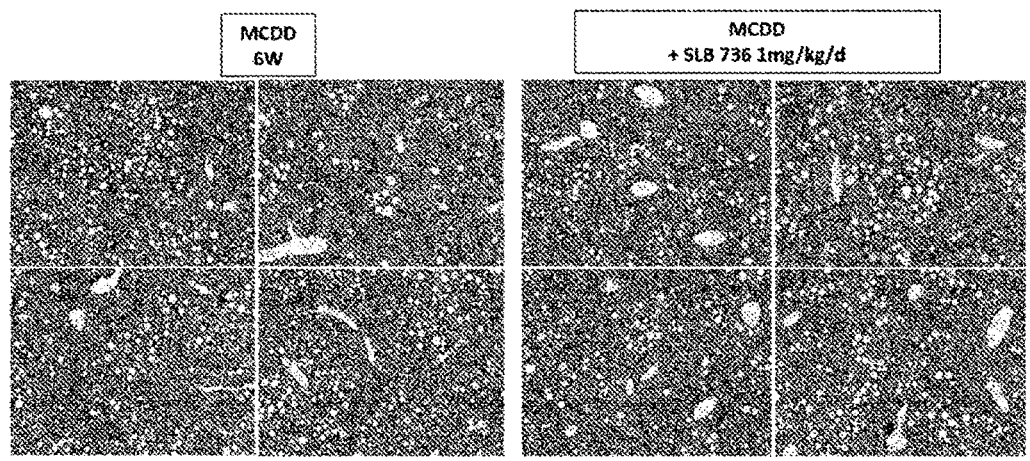
FIG. 8 shows the result of microscopic examination for identifying the effect of SLB736 on the prevention of fibrosis in liver tissue of a NASH-induced mouse model.

Specifically, eight-week-old mice (C57BL6/N, Orient Bio Inc., Korea) were divided into two groups, the control group was fed only with MCDD for 6 weeks to induce the onset of NASH, and the experimental group was fed with SLB736 in a dose of 1 mg/kg/day for six weeks in combination with MCDD, liver tissue was collected from each mouse and was observed with a microscope, and the degree of steatosis, lobular inflammation and fibrosis was observed. The result showed that the degree of steatosis and lobular inflammation (see black triangle in FIG. 7) were significantly reduced in mice administered in combination with SLB736, and the degree of fibrosis was also significantly reduced in the SLB736 administration group.

Figure 9:
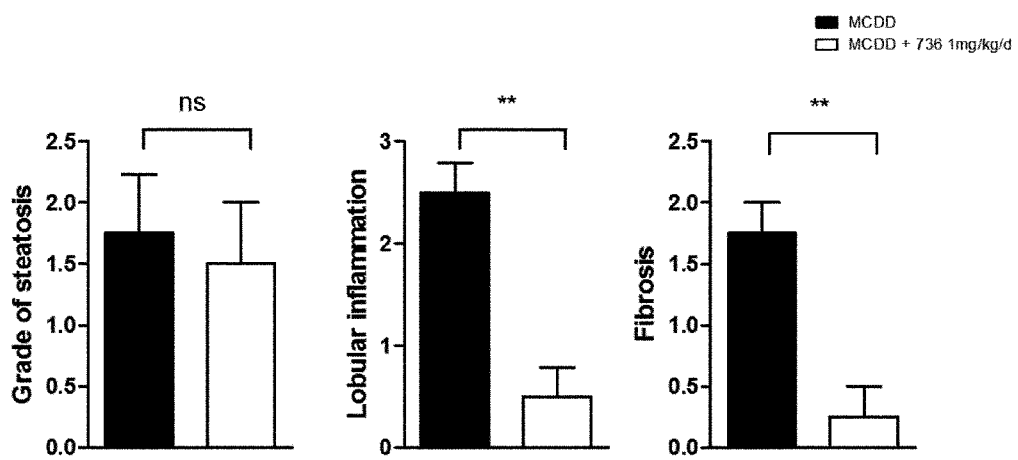
FIG. 9 shows the result of evaluation on the NASH prevention effect of SLB736 in liver tissue of the NASH-induced mouse model based on the CRN scoring system.

In order to determine this quantitatively, evaluation was conducted according to the NAS system of the CRN. The result showed that, as shown in FIG. 9, the degree of steatosis, lobular inflammation and the degree of fibrosis were all significantly alleviated compared to the control group.

Figure 10:
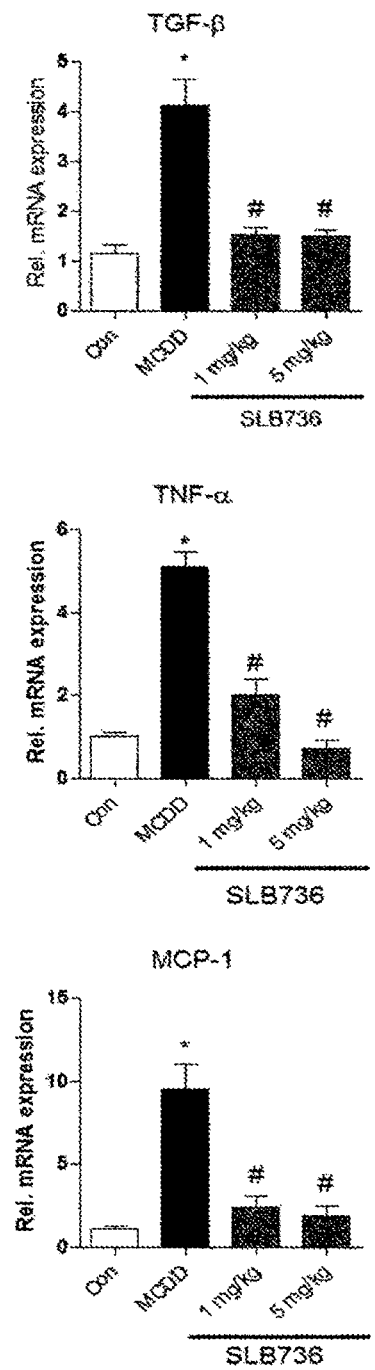
FIG. 10 shows the result identifying the expression inhibition effects of inflammatory and fibrosis markers in liver tissue of the mouse model.

In addition, the expression levels of TGF-β, TNF-α and MCP-1 were measured in order to identify the effects of the SLB736 compound on the expression of inflammatory markers and fibrosis markers in liver tissue. Specifically, RNA was extracted from liver tissue of the animal model and mRNA was measured using Q-PCR. The result showed that the expression of all of TGF-β, TNF-α and MCP-1 was reduced to a significant level in mice administered with SLB736 (FIG. 10).

This shows that the compound SLB736 of the present invention is effective in preventing nonalcoholic steatohepatitis (NASH).

A NASH-induced animal model obtained by administering MCDD to 8-week-old mice (C57BL6/N, Orient Bio Inc., Korea) for 4 weeks was used in order to identify the effect of the SLB736 compound on the treatment of non-alcoholic steatohepatitis (NASH). Specifically, the NASH-induced model mice were divided into two groups, the control group was further fed with MCDD for 4 weeks, the experimental group was fed with SLB736 at a dose of 5 mg/kg/day for 4 weeks in combination with MCDD, and liver tissue was collected from each mouse and observed with a microscope to determine the degree of steatosis, lobular inflammation and fibrosis.

Figure 11A:
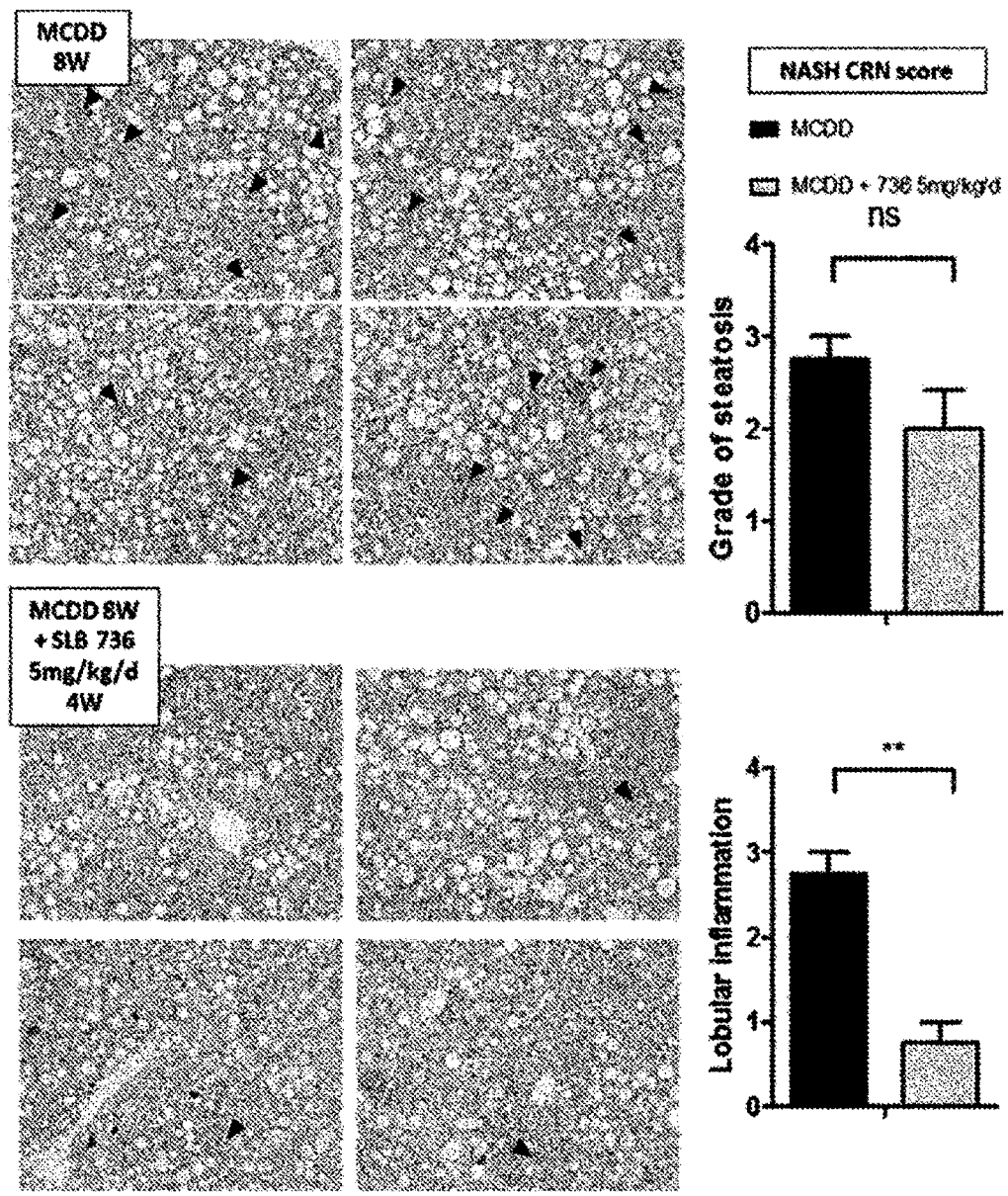
FIG. 11 shows the result identifying the therapeutic effect of SLB736 in liver tissue of the mouse model (A—treatment of steatosis and lobular inflammation; B—treatment of fibrosis)
Figure 11B:
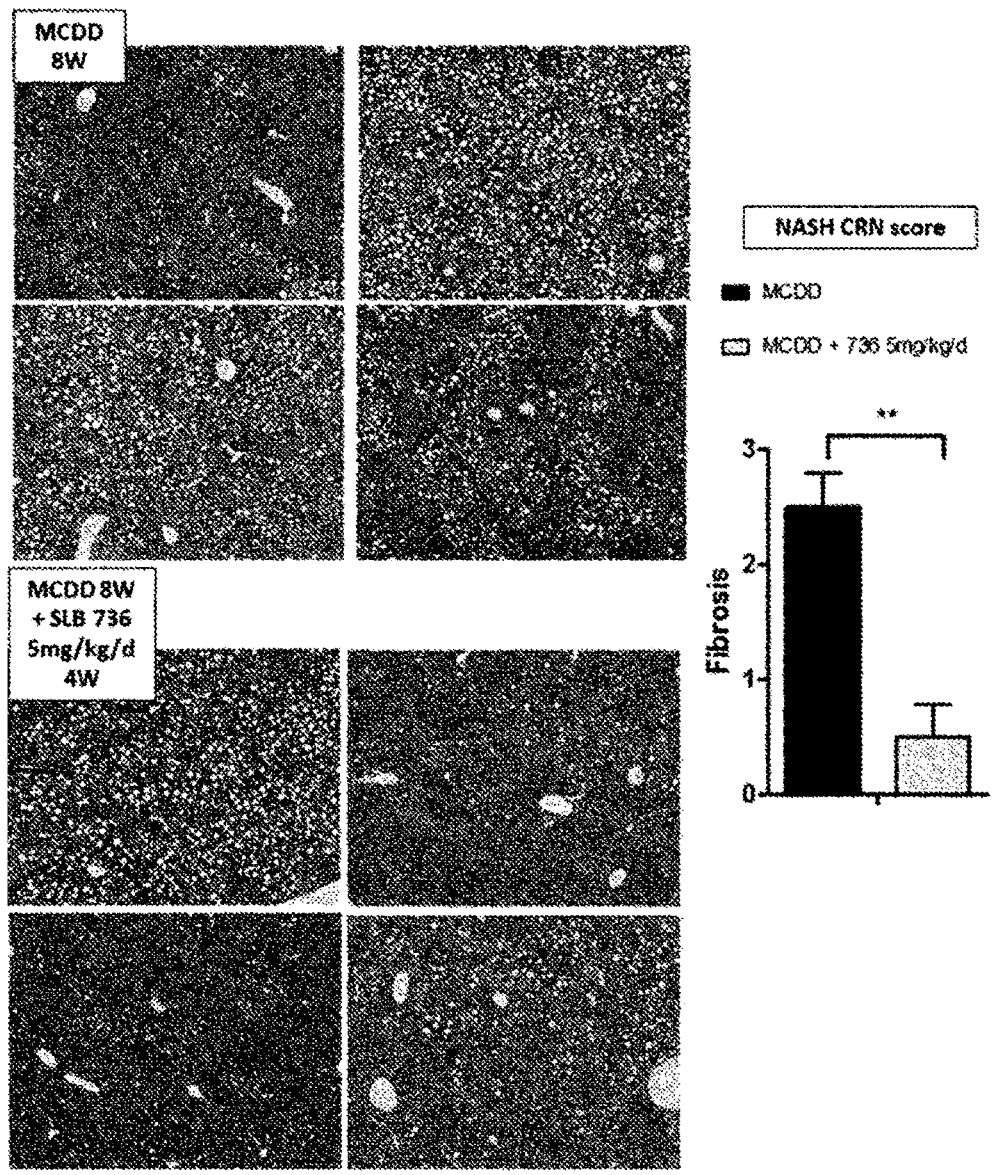

The result showed that the control group that had been continuously fed with MCDD was found to have steatosis, lobular inflammation and fibrosis in liver tissues due to the administration of MCDD, indicating the onset of NASH. On the other hand, the mice administered with SLB736, in combination with a general diet, exhibited a considerable reduction in the degree of steatosis and lobular inflammation (FIG. 11), and the SLB736 administration group also exhibited a considerable reduction in the degree of fibrosis (FIG. 11).

EXAMPLE 7

Comparison of Lymphopenia in Blood Between Administration of SLB736 and FTY720

FTY720, which acts as a functional antagonist of S1PR, has been reported to cause the serious side effect, lymphopenia in the blood. Therefore, when the SLB736 of the present invention was administered, changes of leukocytes and lymphocytes in the blood were measured to determine the possibility of side effects. On the day of autopsy, blood was collected from the posterior vein using a syringe and whole blood was refrigerated in an EDTA-2K CBC bottle. The leukocytes and lymphocytes in the whole blood were measured using an automated analyzer.

Figure 12:
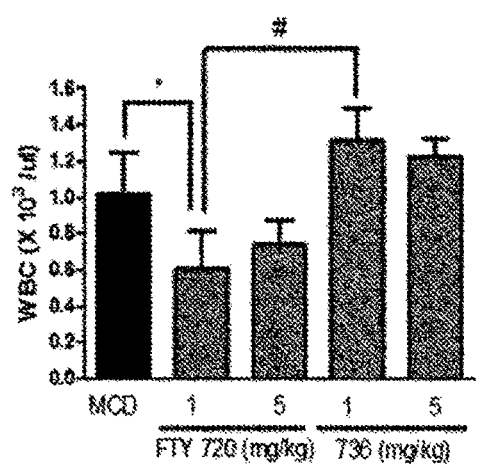
FIG. 12 shows the result identifying that lymphopenia does not appear in blood after administration of SLB736, compared to after administration of FTY720.
Figure 12:
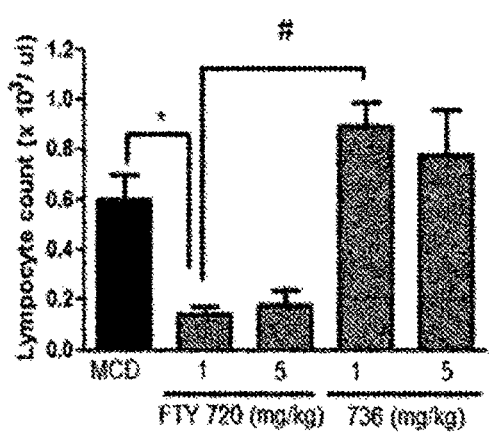

As shown in FIG. 12, the result showed that the mice administered with SLB736 had no reduction of lymphocytes and leukocytes in blood, which means that administration of FTY720 causes no side effects.

What is claimed:

1. A method for treating nonalcoholic steatohepatitis (NASH) comprising administering to a subject a pharmaceutical composition comprising a compound selected from the group consisting of the following compounds, an optical isomer thereof or a pharmaceutically acceptable salt thereof as an active ingredient:
    (1) 2-amino-2-(2-(3-decylisoxazol-5-yl)ethyl)propane-1,3-diol;
    (2) 2-amino-2-(2-(1-decyl-1H-1,2,3-triazol-4-yl)ethyl)propane-1,3-diol;
    (3) 2-amino-2((3-octylisoxazol-5-yl)ethynyl)propane-1,3-diol;
    (4) 2-amino-2-(2-(3-octylisoxazol-5-yl)ethyl)propane-1,3-diol;
    (5) 2-amino-2-(hydroxymethyl)-4-(3-octylisoxazol-5-yl)butyl dihydrogen phosphate;
    (6) 2-amino-2-((3-decylisoxazol-5-yl)ethynyl)propane-1,3-diol;
    (7) 2-amino-4-(3-decylisoxazol-5-yl)-2-(hydroxymethyl)butyl dihydrogen phosphate;
    (8) 2-amino-2-(2-(3-(4-hexylphenethyl)isoxazol-5-yl)ethyl)propane-1,3-diol;
    (9) 2-amino-2((3-dodecylisoxazol-5-yl)ethynyl)propane-1,3-diol;
    (10) 2-amino-2-(2-(3-dodecylisoxazol-5-yl)ethyl)propane-1,3-diol;
    (11) 2-amino-4-(3-dodecylisoxazol-5-yl)-2-(hydroxymethyl)butyl dihydrogen phosphate;
    (12) 2-amino-2-(2-(1-octyl-1H-1,2,3-triazol-4-yl)ethynyl)propane-1,3-diol;
    (13) 2-amino-2-(2-(1-octyl-1H-1,2,3-triazol-4-yl)ethyl)propane-1,3-diol;
    (14) 2-amino-24(1-decyl-1H-1,2,3-triazol-4-yl)ethynyl)propane-1,3-diol;
    (15) 2-amino-2-(2-(1-(4-hexylphenethyl)-1H-1,2,3-triazol-4-yl)ethyl)propane-1,3-diol;
    (16) 2-amino-2-(1-butyl-1H-1,2,3-triazol-4-yl)propane-1,3-diol;
    (17) 2-amino-2-(3-dodecylisoxazol-5-yl)propane-1,3-diol;
    (18) (E)-2-amino-2-(2-(3-decylisoxazol-5-yl)vinyl)propane-1,3-diol;
    (19) (E)-2-amino-2-(1-butyl-1H-1,2,3-triazol-4-yl)propane-1,3-diol;
    (20) 2-amino-2-(2-(3-(8-phenyloctyl)-isoxazol-5-yl)ethyl)propane-1,3-diol;
    (21) 2-amino-2-(2-(1-(8-phenyloctyl)-1H-1,2,3-triazole-butyl-4-yl)propane-1,3-diol;
    (22) N-(2-(1-dodecyl-1H-1,2,3-triazol-4-yl)-1,3-dihydroxypropan-2-yl)acetamide;
    (23) N-(2-(3-dodecylisoxazol-5-yl)-1,3-dihydroxypropan-2-yl)acetamide;
    (24) N-(4-(1-decyl-1H-1,2,3-triazol-4-yl)-1-hydroxy-2-(hydroxymethyl)butan-2-yl)acetamide;
    (25) N-(4-(3-decylisoxazol-5-yl)-1-hydroxy-2-(hydroxymethyl)butan-2-yl)acetamide; and
    (26) N-(4-(1-(4-hexylphenethyl)-1H-1,2,3-triazol-4-yl)-1-hydroxy-2-(hydroxymethyl)butan-2-y1)acetamide.

2. A method for treating nonalcoholic steatohepatitis (NASH) comprising administering to a subject a pharmaceutical composition comprising a compound represented by the following Formula 2 or a pharmaceutically acceptable salt thereof as an active ingredient:

[Formula 2]

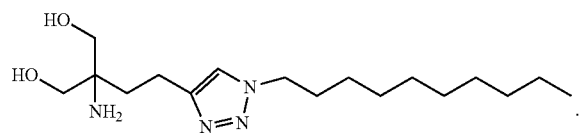

* * * * *